United States Patent [19]
Riley

[11] Patent Number: 5,694,941
[45] Date of Patent: Dec. 9, 1997

[54] PHYSIOLOGICAL WAVEFORM DELAY INDICATOR/CONTROLLER

[75] Inventor: Michael Joseph Riley, Groveland, Mass.

[73] Assignee: Siemens Medical Systems, Inc., Iselin, N.J.

[21] Appl. No.: 674,640

[22] Filed: Jun. 28, 1996

[51] Int. Cl.⁶ .................................................. A61B 5/0402
[52] U.S. Cl. ............................................................. 128/696
[58] Field of Search ................................... 128/696, 710, 128/712

[56] References Cited

U.S. PATENT DOCUMENTS

| | | | |
|---|---|---|---|
| 3,561,428 | 2/1971 | Jacobson | 128/712 |
| 4,356,475 | 10/1982 | Neumann et al. | 340/521 |
| 4,743,966 | 5/1988 | Matsuo | 128/712 |
| 4,804,950 | 2/1989 | Moon et al. | 340/715 |
| 5,253,650 | 10/1993 | Wada | 128/712 |
| 5,319,363 | 6/1994 | Welch et al. | 340/825.36 |
| 5,381,798 | 1/1995 | Burrows | 128/696 |
| 5,400,794 | 3/1995 | Gorman | 128/696 |
| 5,459,725 | 10/1995 | Bodner et al. | 370/60 |
| 5,623,934 | 4/1997 | Midorikawa | 128/696 |

*Primary Examiner*—William E. Kamm
*Attorney, Agent, or Firm*—Lawrence C. Edelman

[57] ABSTRACT

In a patient monitoring system which includes a signal transmission path between that portion of the patient monitoring system which acquires the physiological signals and that portion of the system which processes and displays the acquired signals, a method and apparatus is provided for displaying to a user of the system a time delay that is associated with a delay of the display of the physiological signals.

10 Claims, 4 Drawing Sheets

PHYSIOLOGICAL WAVEFORM DELAY INDICATOR/CONTROLLER

BACKGROUND OF THE INVENTION

1. Field of the Invention

The present invention relates generally to patient monitoring systems which display physiological signals acquired from a patient, and more particularly to a time delay associated with the display of the physiological signals.

2. Description of the Prior Art

Several types of prior art patient monitoring systems typically include a first apparatus for acquiring physiological signals representative of a physiological condition of a patient, and a second apparatus located in an area remote from the first apparatus for signal processing and display of the acquired physiological signals. A signal transmission link is used for transmission of the acquired physiological signals from the first apparatus to the second apparatus.

One such prior art patient monitoring system is shown in U.S. Pat. No. 5,319,363 entitled NETWORK FOR PORTABLE PATIENT MONITORING DEVICES issued to Welch et al., wherein multiple patient care devices suitable for monitoring patients at selected ones of multiple locations are coupled to a common workstation by a network of signal transmission links. The patient care devices include, for example, a plurality of bedside patient monitors interconnected via a local area network (LAN) that conforms to an Ethernet standard and forms part of a wide area network (WAN) which itself is part of the hospital-wide information network that provides for the transmission and storage of various types of patient data throughout the hospital. In addition to the LAN, a wireless radio frequency (RF) network is provided for wireless transmission of patient data to the workstation from portable patient monitoring devices.

One problem encountered in this type of patient monitoring system is occasional loss of the acquired patient data due to electrical interference and/or noise affecting the data transmission network, and in particular wireless portions of a patient monitoring network are particularly susceptible to such interference.

U.S. Pat. No. 5,381,798 entitled SPREAD SPECTRUM TELEMETRY OF PHYSIOLOGICAL SIGNALS issued to Burrows, discloses a conventional patient monitoring telemetry system using the well known spread spectrum modulation technique in conjunction with the wireless transmission of patient data signals from a portable patient data acquiring device to a centrally located signal processing and display device. As described therein, occasional noise or interference associated with the wireless transmission of the patient data can degrade the accuracy of the physiological signals that are reproduced by the display portion of the system. Although the '798 patent describes the application of spread spectrum techniques for improving immunity of the system to interference or noise, such a system is relatively complex and therefore costly. Although less complex systems may be more susceptible to noise or other electrical interference, it is also relatively easy to incorporate interpolation techniques into such systems in order to generate patient data that is approximately correct as a substitute for the data that is occasionally lost. More specifically, a conventional prior art digital electrocardiogram (EKG) system may develop EKG signal samples at 20 msec. intervals. Consequently, loss of 1, 2 or even 5 adjacent signal samples results in the loss of a relatively insignificant portion of an EKG signal waveform, and therefore interpolation techniques can be used in order to reconstruct the original EKG signal without excessive inaccuracies. However, in a more complex patient signal transmission network, such as that described in the '798 patent, such interpolation techniques are not applicable. That is, in the '798 patent, 22 adjacent waveform samples are grouped together in a data frame, and therefore loss of an entire frame of samples necessarily results in loss of a significant portion of the EKG waveform.

Another example of a prior art patient monitoring system including a data transmission network is described by Moon et al. in U.S. Pat. No. 4,804,950 entitled TABLE DRIVEN MULTICHANNEL DATA ACQUISITION AND DISPLAY FOR SIGNAL MONITORING, wherein data packets having 56 samples (bytes) of physiological signal data are used in the data transmission network. Again, in such a system replacement of lost data packets by interpolation techniques would not be acceptable because the loss of a group or packet of signal samples most likely represents loss of a significant portion of the signal information. For example, since the QRS portion of an EKG signal is approximately 100–150 msecs. long, when data packets of 20–50 samples are used, covering an interval of 100–250 msecs., an entire QRS component of an EKG signal can be lost and interpolation techniques will not be sufficient to recover the lost data.

It would be desirable to provide a patient monitoring system having a signal processing and display apparatus that would take into account the occasional loss of transmitted data packets, and still provide an acceptable display of the corresponding physiological signals.

Furthermore, it would be desirable that such a patient monitoring system would not be more costly or complex than a system that does not take into account the occasional loss of data packets.

Thus, it is an object of the present invention to provide a method and apparatus in a patient monitoring system that attempts to mask or otherwise prevent occasional loss of the patient data to result in gaps or other inaccuracies in the display of the patient information.

It is a further object of the invention to provide an indication to the user of the system of a measure of an operating characteristic of the monitor display which is affected by the attempted masking of the data loss.

SUMMARY OF THE INVENTION

In a patient monitoring system which includes a signal transmission path between that portion of the patient monitoring system which acquires the physiological signals and that portion of the system which processes and displays the acquired signals, a method and apparatus is provided for displaying to a user of the system a time delay that is associated with a delay of the display of the physiological signals.

In accordance with one aspect of the invention, in patient monitoring systems using data packets for signal transmission, such a display delay could be useful for introducing a time offset into the signal path of the physiological signals, thereby delaying display of the physiological signals while the receiver of the data packets asks the sender to re-send any data packets that were improperly received. While the receiver is waiting for the re-transmission of the lost data, the display may either be delayed until the improperly received data is finally received, or if the delay time has expired and the replacement data has not yet been received, the display will cause a gap to appear where the improperly received data was to be displayed, and the gap will be "filled-in" at a later time when the data is finally received. Unfortunately, introducing an unknown amount of time delay into a patient information display is generally unacceptable because the user typically believes the display represents substantially real-time conditions. Furthermore, if the display is not delayed, the gap in the displayed data, and later fill-in of the patient data may be visually disturbing.

In accordance with a further aspect of the invention, a user of the patient monitoring system can adjust the time delay of the display of the physiological signals, in order that any patient data lost due to interference can be re-sent to the display from the acquiring device before that portion of the physiological signal having the lost data is applied to the display.

DETAILED DESCRIPTION OF THE PREFERRED EMBODIMENT

Figure 1:
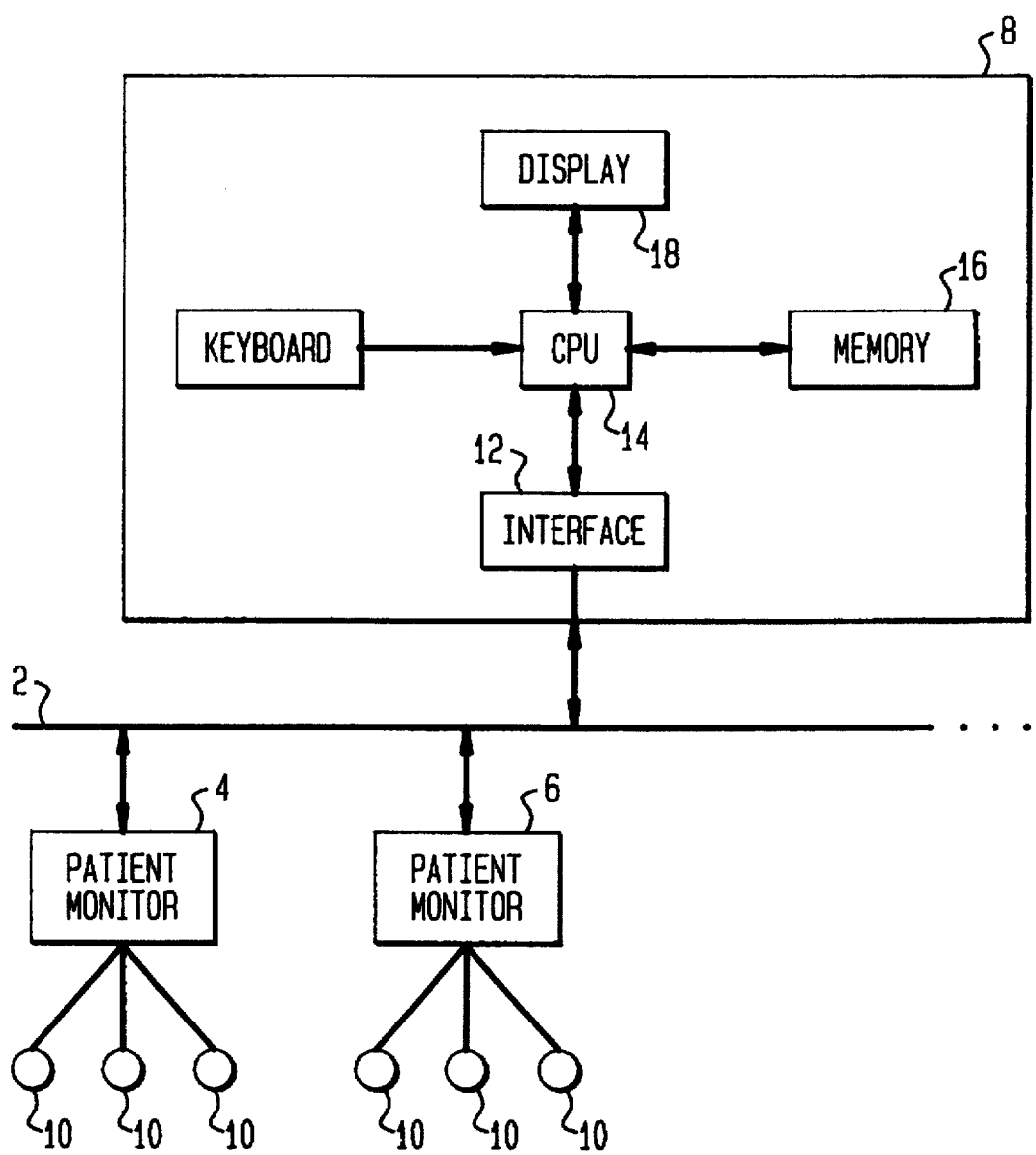
FIG. 1 illustrates one embodiment of a patient monitoring system constructed in accordance with the principles of the present invention.

FIG. 1 illustrates a patient monitoring system of the type that includes a network 2 for the transmission of patient data signals that are acquired by a plurality of patient monitoring devices 4, 6, etc. to a central workstation 8. The patient monitoring devices 4, 6 include a plurality of physiological signal sensors 10 for acquiring physiological signals from a patient (not shown) and providing patient data signals to the data transmission link 2. Patient monitors 4, 6 may comprise conventional bedside monitors for monitoring one or more of heart electrical activity, blood temperature, blood pressure, blood oxygen saturation, etc. using an appropriate physiological signal sensor 10, and developing digital patient data signals in response thereto. The digital patient data signals are provided to a workstation 8 at a nurses station via the hospital data transmission network 2. Alternatively, one or more patient monitors 4, 6 may comprise telemetry transmitters of the type conventionally used to monitor the heart activity of ambulating patients, and the data transmission network 2 may comprise an array of antennas spread throughout the monitoring area and having associated electrical wiring and repeater amplifiers necessary to acquire the RF signals transmitted by telemetry monitors 4, 6 and provide them to the workstation 8. Workstation 8 includes an interface 12 for receipt of the transmitted patient data signals, a CPU 14 and memory 16 which cooperate to process the patient data signals and develop patient physiological signals, and a display 18 for display of the patient physiological signals as numeric and/or waveform information.

Figure 2:
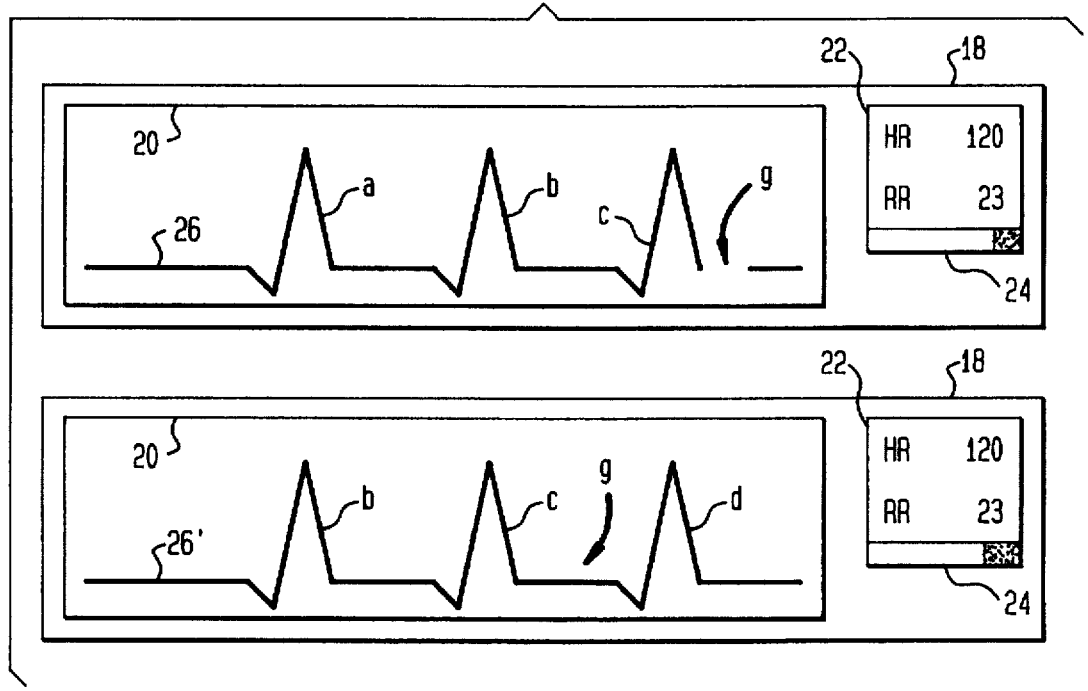
FIG. 2 illustrates one embodiment of the display of FIG. 1, operating in accordance with the principles of the invention.

In this regard, it is noted that there are several types of signal processing delays associated with the patient data signals, so that the patient information appearing on display 18 may actually be displayed 1, 2, 3 or even more seconds delayed, or time offset, from real-time monitoring of the signals from the patient. Such time delays between acquisition and display of the patient information may not be acceptable in certain situations. For example, in the event that the display is a remote display in an operating room which receives the acquired patient data signals via a LAN, if an artery wedge measurement is being undertaken, such a time delay before display of the pressure waveform would be unacceptable. Consequently, the designer of the patient monitoring system could provide for rapid display of the patient information signals with almost no time delay between their signal acquisition and display, however, as previously noted, interpolation techniques may not provide sufficient accuracy to reconstruct the patient data in the event of patient data loss due to noise or electrical interference. In that case, CPU 14 and memory 16 would process the received data packets so as to cause display 18 to display a patient information signal 26, such as shown in FIG. 2, and at the same time CPU 14 of workstation 8 would request that the appropriate of one of patient monitors 4, 6 retransmit a specifically requested patient data packet that was lost. After workstation 8 receives the retransmitted patient data, it can then "update" the display 18 with the missing data.

Such a display of patient data is shown in FIG. 2, wherein the display 18 includes a waveform display area 20 and a parameter display area 22. A waveform delay indicator area 24 is also provided, and may comprise, for example, a horizontal bar whose length is proportional to the amount of time delay applied to the acquired patient data signals before they are displayed. Such a time delay can be easily realized by CPU 14 causing a portion of memory 16 to be used as a shift register type of storage buffer. In a preferred embodiment, the length of the visual indicator bar 24 can be calibrated to the same scale as the horizontal (time) scale used for displaying the EKG waveform in waveform area 20. In the FIG. 2 example, the amount of delay indicated on bar 24 is approximately 1/10th of a complete cycle of the waveform 26 illustrated in waveform area 20.

In operation, due to the user requested short time delay between receipt of the patient data signals by workstation 8 and the display of the patient information on display 18, a gap "g" may appear in the patient information, as indicated in that portion of waveform 26 which follows peak c. After a period of time corresponding to approximately one cycle of patient information, as evidenced by the comparison of the peaks of waveform 26 and 26', the missing data in portion "g" of waveform 26' was properly received by workstation 8, and waveform 26' will suddenly be "filled-in".

This "fill-in" process allows the clinician to see the patient data with minimum delay and without affecting the waveform flow at the viewing device. However, such "updating" of the display by "fill-in" of the missing data may be found objectionable to the users of the patient monitoring device, and therefore, it is a further object of the present invention to provide a method and apparatus for allowing the user to control the amount of delay (time offset) provided to the display of patient information in order to allow workstation 8 to request any patient data signals which were not properly received from network 2, and subsequently receive the requested data and incorporate it into the previously received patient data so that a continuous display, i.e., without gaps in the patient data, can be provided. By providing an operator control of the display delay, the possibly disturbing "fill-in" effect could be substantially avoided. However, the clinician should also be constantly advised of the amount of patient information display delay that results from reducing the "fill-in" display effects, in order to prevent the erroneous belief that the display is substantially in real-time.

Figure 3:
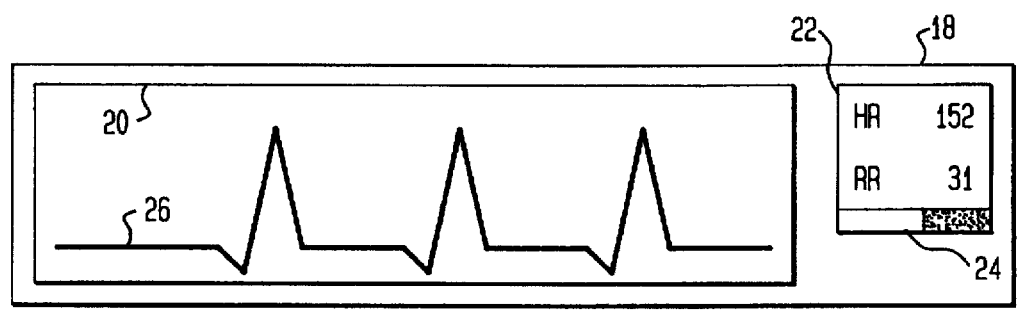
FIG. 3 illustrates a further embodiment of the display of FIG. 1, operating in accordance with the principles of the invention.

Consequently, FIG. 3 illustrates a display 18 wherein the time delay of the display is adjusted to be substantially longer than the delay shown in the FIG. 2 embodiment, i.e., approximately ⅓ of a complete cycle of the waveform 26 illustrated in waveform area 20. Note, that with this delay for the display of the patient information signals, the "fill-in" effects are avoided, yet the user is also advised, by indicator 24, of the amount of the delay.

Figure 4:
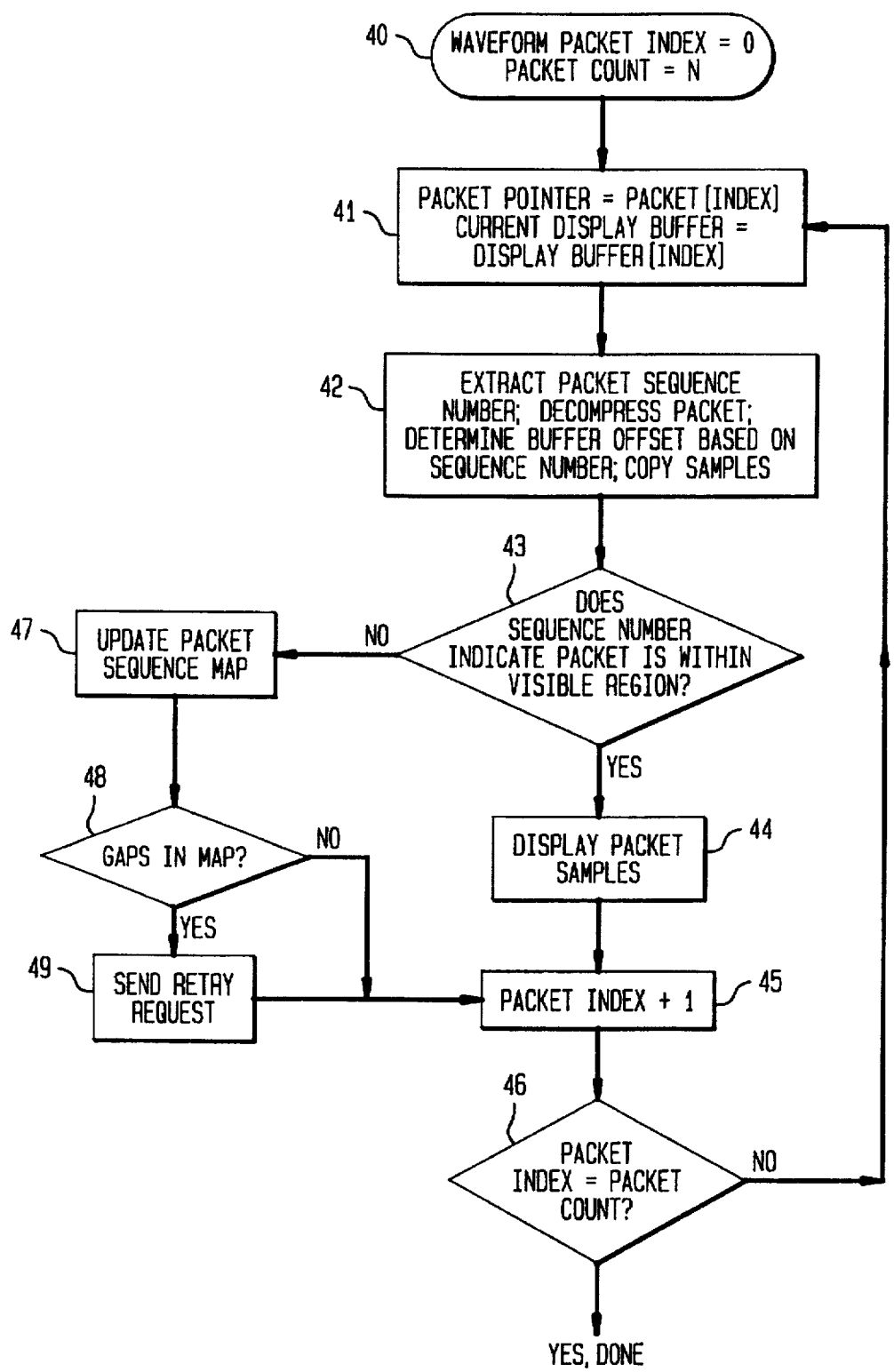
FIG. 4 illustrates a flow chart useful for understanding one aspect of the present invention.

FIG. 4 illustrates in flow chart form operation of CPU 14 for determining proper receipt of the transmitted data packets when they are indicative of, for example, a physiological waveform. Step 40 establishes a starting point for the sequence of waveform packets, such as "index=0", and a total number of packets expected to be received, equal to N. In Step 41 a packet pointer is set to be the current packet, which is initially 0. Additionally, a current display buffer index is set, corresponding to a shift register storage buffer type of processing that establishes where the current data packet will be placed for subsequent display. Step 42 extracts from the current packet its sequence number, such as the fifth packet in a sequence of 56 packets, decompresses the data within the packet, and from the extracted sequence number, determines where in the display buffer (a portion of memory 16), the CPU should store the data packet. The last portion of Step 42 copies the patient data from the packet to the appropriate portion of the display buffer. Step 43 determines if the sequence number extracted from Step 42 is such that, when compared with the display delay time set by the user of the patient monitor, has already resulted in display of patient information from data packets from a sequentially adjacent packet. If the sequence number of the current packet indicates that its sequentially adjacent packets have already been displayed, and thus the display already has a gap corresponding to that portion of the patient information representative of the current data packet, Step 44 causes said packet to be immediately displayed. Step 45 increments the packet index number and Step 46 causes the above process to be repeated if the current packet index number is less than the total number of packets expected to be received.

In the event that Step 44 determines that the sequence number of the current packet is such that its sequentially adjacent packets are not yet being displayed, Step 47 updates a map of the packet sequence, Step 48 determines if there are any gaps in the packet sequence, and if there are no gaps in the sequence, the process moves to Step 45. However, if there is a gap in the packet sequence, Step 49 causes CPU 14 to send a request to the supplier of the data packets, patient monitors 4, 6, to re-send the current packet. Thus, Step 42 also determines any offset that may be required in the positioning of the data packet in the display buffer, in order that the data packet will appear in a proper sequence with the data packets already received and those expected to be received. If an offset is required due to the data packet having a sequence number which is out of order, the result is a gap in the display buffer, resulting in the forenoted gaps "g" in the patient information shown in the top portion of FIG. 2.

Figure 5:
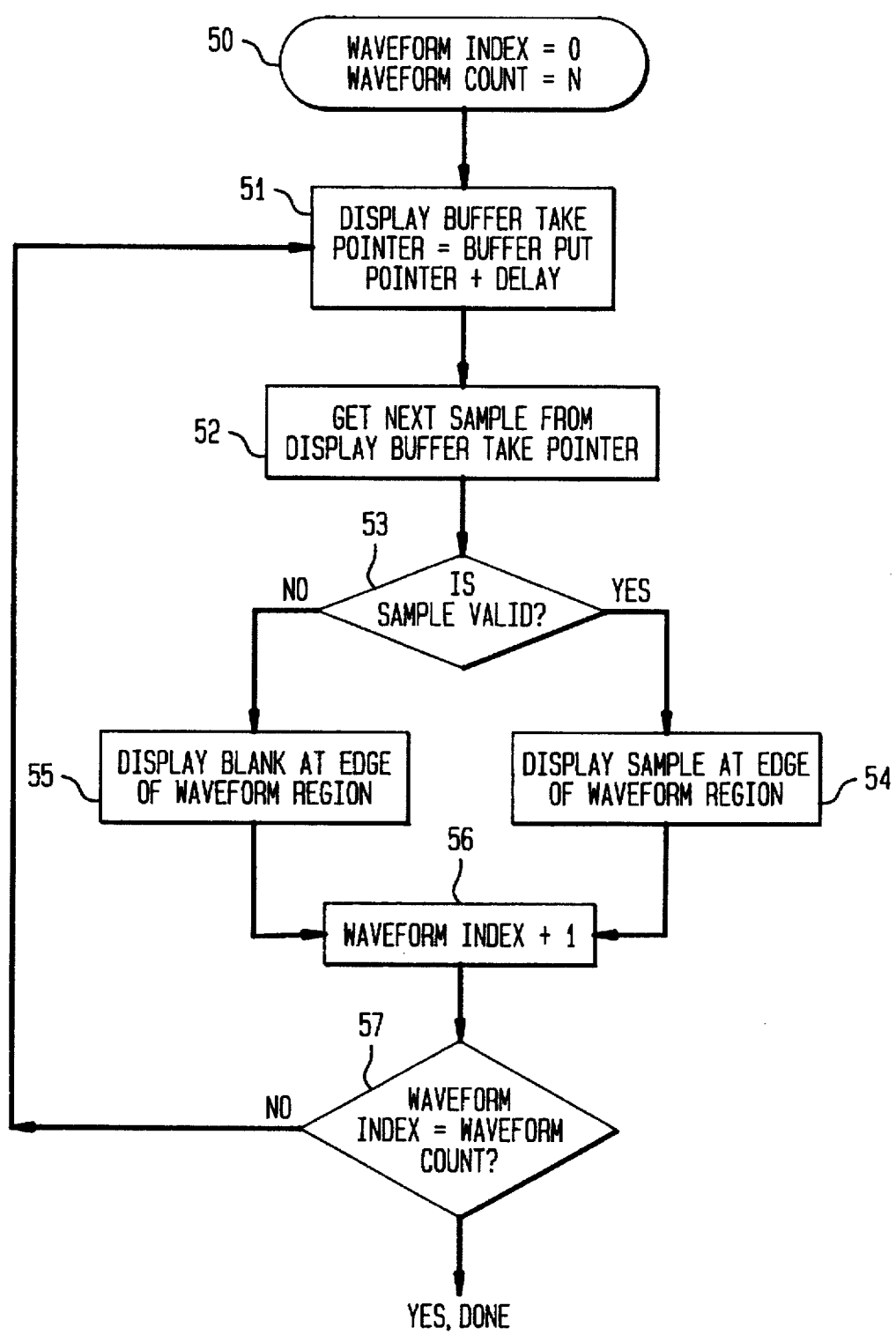
FIG. 5 illustrates a flow chart useful for understanding a further aspect of the present invention

FIG. 5 illustrates the operation of CPU 14 for causing display of the patient information stored in accordance with Step 42 described above.

The procedure about to be described provides for the sequential display of individual points for a plurality of patient waveforms. In this regard, in Step 50 the waveform index is initially set to 0 and the total number of waveforms to be displayed is indicated by the count being equal to "N". In Step 51 a "take" pointer for controlling the taking of waveform data out of the display buffer is set to be equal to the "put" pointer for the display buffer plus an offset amount equal to the time delay associated by either the user or manufacturer of the patient monitoring system for introducing an additional delay into the display of the patient information.

In Step 52 the next sample of patient information is taken from the display buffer using the "take" pointer. Step 53 determines if this sample is valid, i.e., is not a blank or gap. If the sample is valid, then at Step 54 this sample of patient information is displayed at the edge of the waveform region in display 18, assuming that the waveform data is sweeping across display 18. If Step 53 determines that the sample is not valid, Step 55 causes a blank to be displayed at the edge of the waveform region in display 18. Step 56 increments the waveform index by one, and Step 57 determines if the total number of waveforms has been reached. If not, the process is repeated for the next waveform, until a first point has been displayed for each of the plurality of waveforms. After this, the above procedure is repeated for determining the next point in each of the plurality of waveforms being displayed, and so on and so forth.

Thus, what has been shown and described is a new method and apparatus for displaying physiological signals acquired from a patient in a manner that takes into account the possibility of poor transmission of data packets containing the patient information. While a specific embodiment of the present invention has been illustrated and described herein, it is to be realized that modifications and changes will occur to those skilled in the art. For example, although the patient information being delayed in the preferred embodiment is EKG waveform information, other types of waveform information could be delayed, such as blood pressure waveform information. Additionally, the display time delay would also apply equally well to the display of stationary waveforms, or even the display of numeric data. It is therefore to be understood that the appended claims are intended to cover all such modifications and changes as they fall within the true spirit and scope of the invention.

I claim:

1. A patient monitoring system for the acquisition and display of physiological data acquired from a patient, comprising:

a physiological data acquisition means for acquiring physiological data representative of a physiological condition of a patient and for developing digital patient data signals therefrom;

a data transmission link coupled to said physiological data acquisition means for receiving said digital patient data signals therefrom; and a signal processing and display means coupled to said data transmission link for receiving therefrom said digital patient data signals, and processing said signals for developing patient information signals for display of patient information on a display apparatus, said signal processing and display means including a receive processing means which introduces a variable amount of delay time between receipt of the digital patient data signals and initiation of display of said patient information signals, and including a delay indicator means for causing said display apparatus to display a visual indicator of said delay time.

2. The apparatus of claim 1, wherein said receive processing means determines if the digital patient data signals are properly received from said data transmission link, and if not properly received, requests via said data transmission link that said physiological data acquisition means re-send the not properly received digital patient data signals.

3. Apparatus in accordance with claim 2, wherein said patient data is a physiological waveform, and said receive processing means includes a waveform display controller for causing the display of said waveform with a gap in it in an area corresponding to the not properly received digital patient signals, and later fills in the gap with the proper patient data when the receive processing means determines that proper digital patient data signals have been received.

4. Apparatus in accordance with claim 1, wherein said receive processing means includes a user controllable display delay controller for allowing a user to control said variable amount of delay time.

5. Apparatus in accordance with claim 4, wherein said display delay controller is coupled to said delay indicator means for controlling the visual indicator of time delay in response to user control of said display controller.

6. Apparatus in accordance with claim 5, wherein said patient data is a physiological waveform, and said display delay controller may cause the display of said waveform with a gap in it in an area corresponding to not properly received digital patient data signals and later fills in the gap with proper patient data when proper digital patient data signals have been received; and wherein said display delay controller is controllable by said user to introduce said delay time as a time offset into said waveform display, thereby delaying display of said waveform until proper digital patient data signals are received so that said waveform can be displayed without gaps, and providing a visual indicator on said display means.

7. Apparatus in accordance with claim 1, wherein said patient data is a physiological waveform, and said receive processing means includes a waveform display delay controller which may cause the display of said waveform with a gap in it in an area corresponding to not properly received digital patient signals, and later fills in the gap with proper patient data when proper digital patient data signals have been received; and wherein said display delay controller is controllable by said user to introduce said delay time as a time offset into said waveform display, thereby delaying display of said waveform until proper digital patient data signals are received, so that said waveform can be displayed without gaps.

8. A patient monitoring system for the acquisition and display of physiological data acquired from a patient, comprising:

a physiological data acquisition means for acquiring physiological data representative of a physiological condition of a patient and for developing a sequence of digital patient data signals therefrom;

a data transmission link coupled to said physiological data acquisition means for receiving said sequence of digital patient data signals therefrom; and a signal processing and display means coupled to said data transmission link for receiving said digital patient data signals therefrom, and processing said signals for developing a corresponding sequence of patient information signals for display on a display apparatus, wherein said signal processing and display means includes a receive processing means for determining if the digital patient data signals are properly received from said data transmission link, and if not properly received, requesting via said data transmission link that said physiological data acquisition means re-send that portion of the sequence of the digital patient data signals that was not properly received; and a user controllable display delay controller for introducing a controllable time delay to the start of display of a sequence of said patient information signals on said display, the purpose of said time delay being to allow additional time for receipt by said signal processing and display means of said re-sent digital patient data signals, and insertion of a portion of the sequence of patient information signals corresponding to said re-sent digital patient data signals into said sequence of patient information signals that were properly received, before said sequence of patient information signals is started to be displayed.

9. Apparatus in accordance with claim 8, wherein said display means includes a delay indicator, said display delay controller being coupled to said delay indicator for developing on said display a visual indicator of said time delay in response to user control of said display delay controller.

10. Apparatus in accordance with claim 9, wherein said patient data is a physiological waveform, and said receive processing means includes a waveform display controller for causing display of said waveform with a gap in it in an area corresponding to the not properly received digital patient data signals if said display time delay does not provide a time offset sufficient for receipt of said re-sent digital patient data signals, and later fills-in the gap with the proper patient information signals when said re-sent digital patient data signals have been properly received.

* * * * *